United States Patent [19]
Gilbert

[11] Patent Number: 5,882,599
[45] Date of Patent: Mar. 16, 1999

[54] DILUTER

[75] Inventor: Ian Gilbert, St. Albans, Great Britain

[73] Assignee: Counting Technology Limited, St. Albans, Great Britain

[21] Appl. No.: 716,246

[22] PCT Filed: Mar. 15, 1995

[86] PCT No.: PCT/GB95/00550

§ 371 Date: Mar. 24, 1997

§ 102(e) Date: Mar. 24, 1997

[87] PCT Pub. No.: WO95/25269

PCT Pub. Date: Sep. 21, 1995

[30]  Foreign Application Priority Data

Mar. 15, 1994 [GB] United Kingdom .................. 9405028

[51] Int. Cl.⁶ .............................. B01L 3/00; B01L 11/00
[52] U.S. Cl. ........................ 422/100; 422/82.01; 422/99; 422/81; 436/179
[58] Field of Search ............................ 422/82.01, 82.02, 422/99, 100; 436/179

[56]  References Cited

U.S. PATENT DOCUMENTS

| | | | |
|---|---|---|---|
| 2,656,508 | 10/1953 | Coulter | 324/71 |
| 2,712,624 | 7/1955 | Beattie | 318/306 |
| 2,977,199 | 3/1961 | Quittner | 23/230 |
| 3,186,800 | 6/1965 | Strickler | 23/253 |
| 3,192,017 | 6/1965 | Kruger | 23/253 |
| 3,301,189 | 1/1967 | Kling | 103/38 |
| 3,398,689 | 8/1968 | Allington | 103/11 |
| 3,523,546 | 8/1970 | Berg | 137/240 |
| 3,525,592 | 8/1970 | Buckley | 23/253 |
| 3,661,460 | 5/1972 | Elking et al. | 356/36 |
| 3,740,143 | 6/1973 | Groner et al. | 356/39 |

(List continued on next page.)

FOREIGN PATENT DOCUMENTS

| | | |
|---|---|---|
| 0036566 | 9/1981 | European Pat. Off. . |
| 0046345 | 2/1982 | European Pat. Off. . |
| 0055483 | 7/1982 | European Pat. Off. . |
| 0101161 | 2/1984 | European Pat. Off. . |
| 0159243 | 10/1985 | European Pat. Off. . |
| 0449692 | 1/1995 | European Pat. Off. . |
| 2142502 | 1/1973 | France . |
| 2327543 | 5/1977 | France . |
| 390502 | 2/1924 | Germany . |
| 408499 | 1/1925 | Germany . |
| 1498960 | 6/1969 | Germany . |
| 2031336 | 5/1971 | Germany . |
| 7308698 | 12/1974 | Netherlands . |
| 903156 | 8/1962 | United Kingdom . |
| 1232701 | 5/1971 | United Kingdom . |
| 1436891 | 5/1976 | United Kingdom . |
| 1476209 | 6/1977 | United Kingdom . |
| 2035568 | 6/1980 | United Kingdom . |
| 1590898 | 6/1981 | United Kingdom . |
| 1598078 | 9/1981 | United Kingdom . |
| 2095403 | 9/1982 | United Kingdom . |
| 0873092 | 5/1987 | WIPO . |

*Primary Examiner*—Robert Warden
*Assistant Examiner*—Fariborz Moazzam
*Attorney, Agent, or Firm*—Baker & Botts, L.L.P.

[57]  ABSTRACT

A fluid diluter has a hydrodynamic focusing device with a circular mixing chamber opening into a receiving chamber via a sensing aperture. Diluent is supplied from a source and mixed with a sample of blood, for example, and the sensing aperture counts the presence of particles such as hemoglobin in the sample using the impedance method. The receiving chamber is subsequently emptied and the cycle repeated. In one embodiment, through-flow is achieved via a pair of pumps having different pumping capacities, connected together with a common actuator rod between the two pistons. In a second embodiment, four pumps are employed, three of which are ganged together. The system is substantially less bulky than known diluters yet permits accurate attainment of high dilution ratios. Particles may be analyzed in the aperture one at a time without coincidence. Altering relative capacities of the pumps permits adjustment of the dilution ratio.

12 Claims, 2 Drawing Sheets

U.S. PATENT DOCUMENTS

| | | | |
|---|---|---|---|
| 3,743,424 | 7/1973 | Coulter | 356/73 |
| 3,746,976 | 7/1973 | Hogg | 324/71 |
| 3,793,587 | 2/1974 | Thom et al. | 324/71 CP |
| 3,810,010 | 5/1974 | Thom | 324/71 CP |
| 3,831,618 | 8/1974 | Liston | 137/154 |
| 3,838,601 | 10/1974 | Dorman | 73/401 |
| 3,848,470 | 11/1974 | Hargash et al. | 73/425.6 |
| 3,871,770 | 3/1975 | Von Behrens et al. | 356/103 |
| 3,900,290 | 8/1975 | Hornstra | 23/230 B |
| 3,925,018 | 12/1975 | Saunders | 23/230 R |
| 3,989,381 | 11/1976 | Fulwyler | 356/39 |
| 4,001,678 | 1/1977 | Berg | 324/71 CP |
| 4,014,611 | 3/1977 | Simpston et al. | 356/72 |
| 4,015,628 | 4/1977 | Randolph | 137/566 |
| 4,019,134 | 4/1977 | Hogg | 324/71 CP |
| 4,050,904 | 9/1977 | Cramer | 23/288 E |
| 4,070,617 | 1/1978 | Kachel et al. | 324/71 CP |
| 4,087,209 | 5/1978 | Mahig et al. | 417/268 |
| 4,120,202 | 10/1978 | Range et al. | 73/421 R |
| 4,120,657 | 10/1978 | Nagy et al. | 23/230 |
| 4,135,825 | 1/1979 | Kertscher | 366/79 |
| 4,165,484 | 8/1979 | Haynes | 324/71 CP |
| 4,198,160 | 4/1980 | Kachel et al. | 356/72 |
| 4,253,058 | 2/1981 | Kachel et al. | 324/71 |
| 4,274,453 | 6/1981 | Lee | 141/1 |
| 4,315,754 | 2/1982 | Ruzicka et al. | 23/230 R |
| 4,394,372 | 7/1983 | Taylor | 424/85 |
| 4,428,669 | 1/1984 | Bessis | 356/39 |
| 4,607,526 | 8/1986 | Bachenheimer et al. | 73/432 PS |
| 4,695,431 | 9/1987 | Farrell | 422/81 |
| 4,972,137 | 11/1990 | Dunstan et al. | 324/71.4 |

DILUTER

This invention relates to a fluid diluter. The invention is particularly, though not exclusively, applicable to a fluid diluter for particle analysis applications.

The person skilled in the art of particle analysis will be aware of the Impedance or Coulter Aperture method of particle counting and sizing. In relation to the analysis of blood cells this method is described in U.S. Pat. No. 2,656,508. For use with powders the method is defined in British Standard BS 3406 pt5.

In the field of haematology the method involves diluting a sample of whole blood in an electrically conductive solution and passing the dilution through a very small hole that has an electric current passing across it. The individual blood cells obscure the hole as they pass and change the current. This current change is a very accurate measure of cell volume and is used to analyse the number and size distribution of red, white and platelet cells in the original sample.

The conventional instrument used in this method has to perform precision dilution of the sample. For example, after a chemical agent has been used to destroy the red cells in a sample of blood, the resulting dilution (typically 250:1) is sent to a white cell counting chamber where the white cells are counted. As there are considerably more red cells than white, the red cell dilution is usually more than 6000:1. This dilution is typically reached by two successive dilutions to preserve accuracy. The dilution of the red cells is sent to a second chamber for counting of the red cells and platelets. After this, all of the chambers and tubes are flushed with clean diluent for minimum contamination of one sample by a previous one. Contamination in this way is commonly known as 'carryover'.

The dilution ratios are necessary as the cells must be far enough apart to be counted individually as they pass through the aperture. If particles are too close together in the diluent, an effect termed 'coincidence' may occur when two or more cells together are sensed in a distorted reading of the current across the aperture.

One of the problems associated with this technique is the difficulty in making accurate dilutions. Such large dilution ratios allow a very small margin for error and are difficult to maintain. Various methods of dilution have been used. A typical example employs precision pipettes. However, they are bulky, as they require a mechanism to move the pipette nozzle from the sample container to a bath where the pipette's exterior can be washed and a precision volume discharged from its interior. Furthermore, this washing must be done in an open bath which, though shrouded, still presents a risk of infection from, for example, hepatitis and HIV from any blood aerosol release into the atmosphere. Many other types of dilution means are used, such as ceramic plate valves with loops, precision flow measurement means, bellows systems, bubble manometers and precision pressure systems. All tend to be expensive and bulky. Several do not take account of the viscosity of the liquids changing when the temperature changes. Those skilled in the art will be familiar with these various dilution methods and their limitations.

The standard method of counting particles involves sucking them through an aperture in a random fashion from a dilution. Electrical current distribution in the aperture is not uniform across its diameter. When cells pass close to the walls of the aperture they are sensed as being larger than those particles that pass straight through the middle of the aperture. There has been a considerable amount of work done to reduce these errors electronically. This is usually termed editing.

It would be desirable to be able to make every particle follow the same path through the aperture. This is known as hydrodynamic focusing which involves directing the diluted sample such that it flows through the centre of the aperture and does not travel close to the walls. A sheath of particle-free diluent is arranged to flow coaxially round the tip or mouth of a tube or orifice—termed a director. The diluted sample is arranged to exit the tube at the same speed as the passing clean diluent and, surrounded by it in the sheath, flows towards the centre of the aperture through which it passes. The velocity of the sample and sheath must match at the point they join otherwise turbulence occurs and the hydraulic alignment may be lost. As long as the two flows are aligned before they reach the aperture then the relationship between the sheath fluid and the sample fluid is maintained throughout transit of the aperture.

The dilution ratio of the system is the ratio of the sample to the particle-free flows as they travel through the aperture. The principle is illustrated in FIG. 1 of the drawings in which the diluted sample flows out of the director and is met by a vortex of diluent creating the sheath which entrains the diluted sample to flow through the centre of the aperture.

To those familiar with the art of small scale fluid flow, it will be appreciated that there will be practical limits to the ratio between sample and sheath. This will be dependent on the relative densities of the sample material and its diluent. Heavier particles will simply sediment out of the diluted sample into the sheath fluid if flow velocities are not high enough. Similarly, the fluid velocities need to be kept up so that the sample travels across the aperture at a reasonable speed. Very high ratios, say 100:1, will only be possible with extremely accurate control of the fluid flows, whereas very low ratios become of no practical use when the sample is allowed to travel close to the aperture walls.

According to the present invention there is provided a fluid diluter comprising at least first and second pump assemblies of respectively smaller and larger pumping capacity for a given pump cycle, storage means for containing the fluid to be diluted, a first conduit for connection to a diluent supply, mixing means arranged to receive the fluid and the diluent, the first pump assembly being arranged to pump the diluent to the mixing means, a receiving conduit for the mixed fluids communicating with the second pump assembly, the delivery stroke of the first pump assembly being arranged to coincide with the charge stroke of the second pump assembly, such that the fluid to be diluted is drawn out of storage means by the second pumping means as the diluent is pumped.

Preferably, the pump assemblies each comprise displacement pumps. The pumping capacity may be variable by adjustment of the pump stroke or by the use of one of a selection of pump fluid displacer members of different volume per unit length of stroke.

Preferably, the mixing means comprise fluid and diluent conduits connected at a mixing junction at first ends and communicating with the storage means and the output of the first pump assembly at second respective ends thereof, the first ends commonly communicating with the input of the second pump assembly. In this form of the invention two or more diluent conduits may be provided which communicate with the mixing means at relatively upstream and downstream locations.

The mixing means may also comprise a hydrodynamic focusing device including an inducting tube or director having one end communicating with the storage means and a focusing chamber communicating with the output of the first pump assembly, the chamber having an aperture at which the other end of the director is directed, the aperture communicating the focusing chamber with the receiving conduit. The diluter may include valve means for regulating the flow to and from the first and second pump assembly. These may be shut-off valves, for example, or non-return valves.

Advantageously, the pump assemblies are differentially actuated by a common actuator.

The invention also extends to a particle analyser including a diluter as described above.

The particle analyser including a diluter as described above and including a hydrodynamic focusing device may have analyser electrodes which are respectively located upstream and downstream of the said aperture.

The invention can be put into practice in various ways some of which will now be described by way of example with reference to the accompanying drawings in which.

Figure 2:
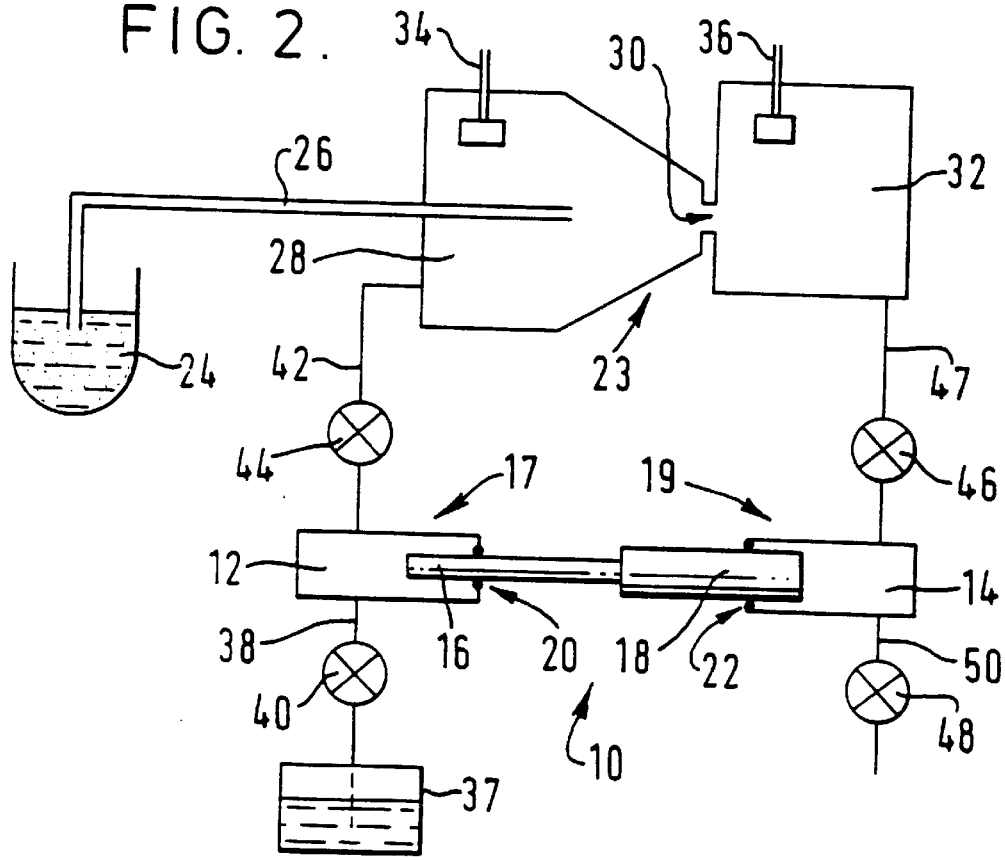
FIG. 2 is a schematic circuit diagram of a first embodiment of the invention.

Referring to FIG. 2, a diluter comprises a double acting pump 10 having first and second cylinders 12 and 14 in which ride a small and a large diameter piston rod 16 and 18, respectively, providing relatively low and high capacity pumps 17 and 19. The piston rods 16 and 18 are fixed together such that they are not movable relative to one another. The internal diameter of each cylinder 12 and 14 is considerably greater than the outside diameter of its associated piston rod such that the latter are a clearance fit within the former.

The projection of the piston beyond the axial extent of its cylinder is sealed by means of seals 20 and 22. Displacement of fluid by the double acting pump 10 is effected by the changing volume as each piston moves.

Figure 1:
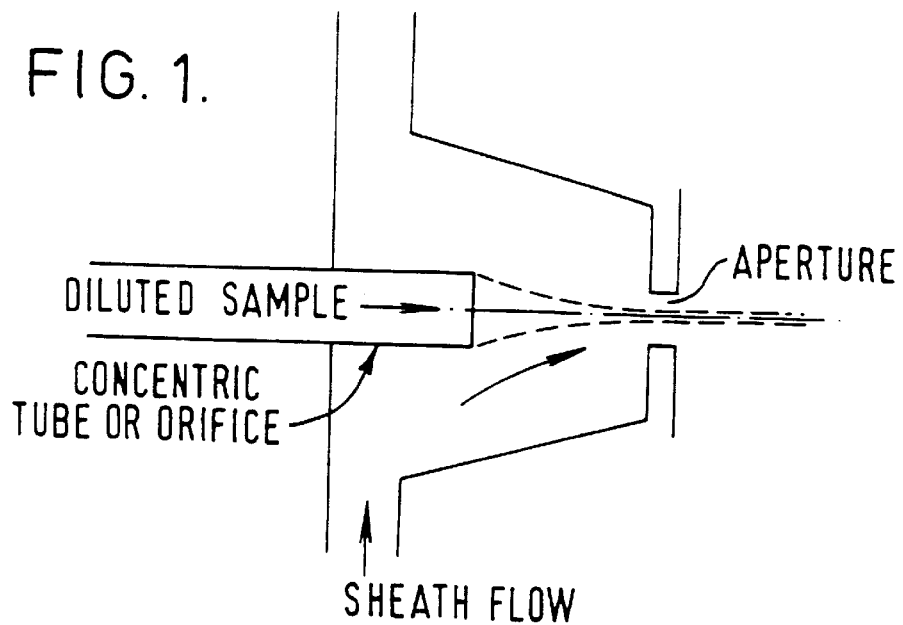
FIG. 1 is an illustration of sheath and sample fluids in relation to an aperture.

A hydrodynamic focusing device 23, similar to that illustrated in FIG. 1, is supplied with a sample to be diluted from a sample container 24 by means of a central tube 26 which constitutes a director for aiming the sample.

The focusing device comprises a circular mixing chamber 28 which tapers to a sensing aperture 30. The side of the aperture opposite the mixing chamber 28 opens out into a receiving chamber 32. Electrodes 34 and 36 are arranged in the mixing chamber 28 and the receiving chamber 32 to count the presence of particles in accordance with the Impedance method. Typically the electrode 34 is earthed and a power source and particle analysis means are connected to the electrode 36.

The diluent is supplied from a source 37 through the low capacity pump 17. A supply line 38 from the source of the diluent to the first cylinder 12 has a shut-off valve 40 in it. Similarly, a delivery line 42 between the cylinder 12 and the inlet to the mixing chamber 28 is provided with a shut-off valve 44.

The receiving chamber 32 is connected to the input to the cylinder 14 of the high capacity pump 19 through a shut-off valve 46 in a line 47. The outlet from the high capacity pump 19 is connected to a further shut-off valve 48 through a line 50.

Delivery of the diluent providing the sheath flow is effected by the pumping stroke of the low capacity pump 17. The valve 40 is closed on the supply line 38. The valve 44 in the delivery line 42 is open.

Simultaneously with the pumping stroke of the low capacity pump 17, the high capacity pump 19 is on its priming or charging stroke, drawing the analysed diluent from the receiving chamber 32 through the open valve 46. The valve 48 on the outlet side of the high capacity pump 19 is closed. It will be clear that the volume of fluid drawn in by the priming high capacity pump 19 will be greater than that delivered by the low capacity pump 17 for a given stroke. The difference is made up by the sample drawn from the sample container 24.

The diluent travels through the mixing chamber 28 and past the end of tube 26 as it is drawn towards the sensing aperture 30. This creates a co-axial sheath of diluent in which the sample is entrained to pass accurately and consistently through the centre of the aperture 30.

At the end of the pump stroke of the pump 17 or before then if the analysis is completed, the open valves 44 and 46 are closed and the valves 40 and 48 are open. The return stroke will thus prime the pump 17 from the diluent source 37 and allow the pump 19 to discharge while the remainder of the system is isolated from the pumping and priming actions. This cycle may be repeated as necessary.

For the purposes of analysing red blood cells a typical ratio of sample to diluent is 6000:1. It is required to separate the individual cells under study sufficiently so that they can be analysed in the aperture one at a time. Such a high ratio is impracticable to realise in one dilution step. To overcome this the dilution may be effected in multiple stages in the same line. This may be by means of the same pump or separate pumping stages possibly of different capacities.

It is possible to vary the dilution ratio by altering the relative capacities of the high and low capacity pumps. Conveniently, this could be achieved by using piston rods of different diameters. In this way the effective volume displaced per unit of stroke travel will be changed.

Figure 3:
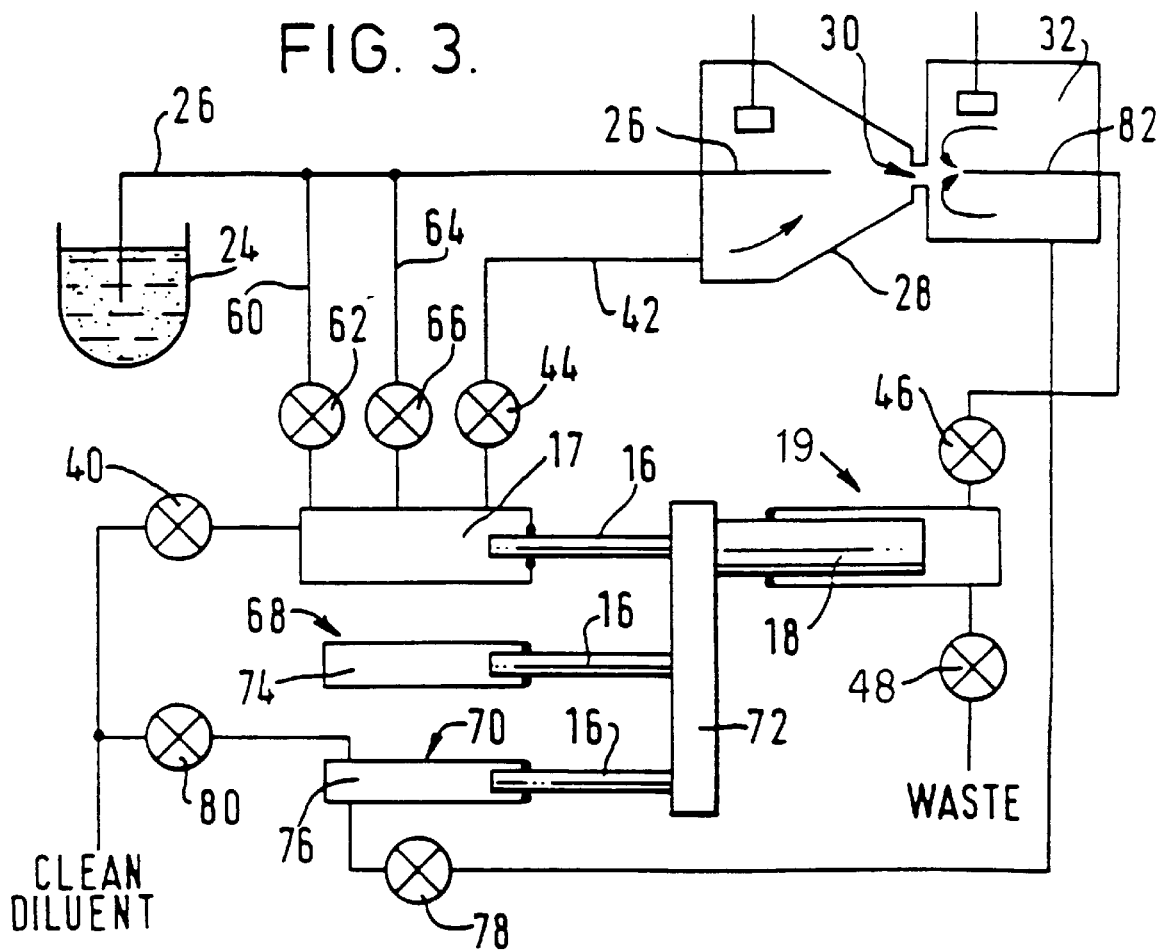
FIG. 3 is a schematic circuit diagram of a second embodiment of the invention.

Turning now to FIG. 3, a modification of the previous embodiment allows multiple stages of mixing and an active co-axial withdrawal of the analysed dilution directly from the rear of the aperture. In relation to FIG. 2, like numerals have been used to denote like parts.

In this embodiment, the mixing is effected at two junctions in the central tube forming the director tube 26 connected to the sample container 24. The first mixing stage comprises a line 60 connected to the cylinder 12 of the low capacity pump 17 and to the tube 26 downstream of the sample container 24. The line 60 has a shut-off valve 62.

A second line 64 is connected between the cylinder 12 and the tube 26. This provides a second mixing stage. Again, the line 64 is provided with a shut-off valve 66. As with the FIG. 2 embodiment, the apparatus also has a delivery line 42 between the cylinder 12 and the inlet to the mixing chamber 28.

Further piston rods of auxiliary pumps 68 and 70 are ganged with the piston rods 16 by their connection to a common actuating bar 72. The pumps 68 and 70 are similar in construction to those previously described although the internal volumes of the cylinders 74 and 76 are smaller. The pump 68 is shown unconnected simply to illustrate that a plurality of such pumps could be ganged together to be put to various uses. For example, the pump 68 could be arranged to provide a flushing facility for the end of the central tube 26 inserted in the sample container. When such flushing takes place the sample container 24 would be removed and replaced by a waste receptacle.

The pump 70 delivers fluid through an open shut-off valve 78 to the receiving chamber 32 during the pumping stroke of the pump 17. At this time the valve 80 in the supply line from the diluent to the pump 70 is closed. The receiving chamber 32 has a circular section internal wall which creates a coaxial flow of clean diluent with respect to the aperture 30. This entrains the dilution fluid flow through the aperture 30 to enter a coaxially located receiving tube 82 close behind the aperture 30 which is connected through the shut-off valve 46 to the inlet to the high capacity pump 19.

At the end of the pump stroke of the pump 17 or before this if sufficient fluid has passed through the aperture for the purposes of analysis, the valve 80 is opened along with the valve 40. The valve 78 is closed in keeping with the valves 62, 66 and 44.

The subsequent priming stroke of the low capacity pump 17 also serves to draw diluent into the pump 70 ready for the next pumping stroke. As before, the valves 46 and 48 associated with the high capacity pump are respectively closed and open for the return stroke to expel the extracted dilution to waste.

It will be noted that the diameter of the piston rod 18' is considerably larger than its equivalent in FIG. 2. This is to take account of the increased volume of fluid to be drawn off as a result of the diluent used to entrain the flow of dilution in the aperture.

The valves associated with the pumping and priming strokes of the pumps could be implemented as conventional non-return valves or specifically actuatable valves under the control of actuators programmed to execute the necessary sequence.

Figure 4:
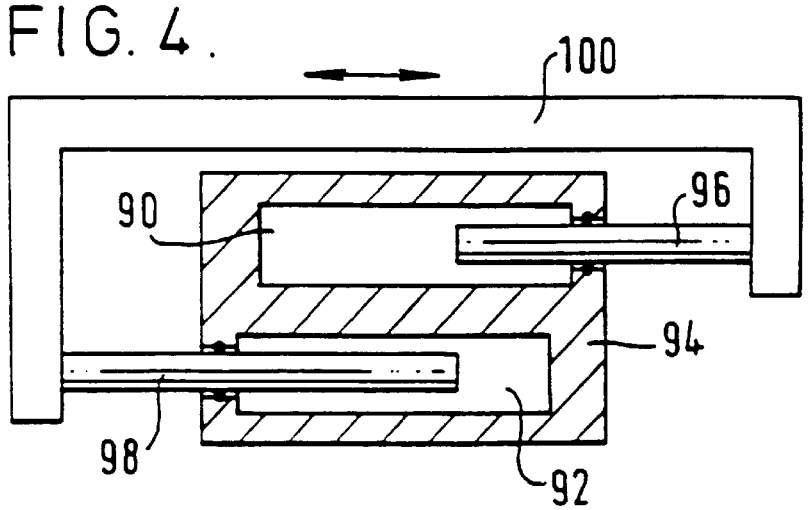
FIG. 4 is a schematic diagram of an alternative pumping arrangement for a diluter according to the invention.

FIG. 4 illustrates a space efficient implementation of a double acting pump assembly in which cylinders 90 and 92 are formed in a common block 94, each extending from an opposite face of the block. Pistons 96 and 98 associated with the block are both connected to a common actuating bar 100.

I claim:

1. A fluid diluter comprising:
    at least first and second pump assemblies wherein the first and second assemblies are of different pumping capacities for a given pump cycle, each of said pump assemblies having a charge stroke and a deliver stroke,
    storage means for containing fluid to be diluted,
    a first conduit for connection to a diluent supply,
    mixing means arranged to receive said fluid and said diluent and to form a mixed fluid, said first pump assembly being arranged to pump said diluent to said mixing means,
    a receiving conduit for said mixed fluid communicating with said second pump assembly,
    said delivery stroke of said first pump assembly being arranged to coincide with said charge stroke of said second pump assembly, such that fluid to be diluted is drawn out of said storage means by said second pump assembly as said diluent is pumped,
    said first and second pump assemblies in turn comprising first and second cylinders and respective first and second pistons therein, said first and second pistons each being sealed with a respective one of said first and second cylinders only at one predetermined portion of said respective cylinder, said first and second pistons being mounted integrally with a common actuator rod connected between them so as not to be movable relative to one another.

2. A fluid diluter as claimed in claim 1, wherein said pump assemblies each comprise displacement pumps.

3. A fluid diluter as claimed in claim 1, wherein said different pumping capacities of said first and second pump assemblies are variable by adjustment of said delivery stroke.

4. A fluid diluter as claimed in claim 1, wherein said pumping capacities are variable by use of one of a selection of pump fluid displacer members of different volumes per unit length of stroke.

5. A fluid diluter as claimed in claim 1, wherein said mixing means comprises fluid and diluent conduits connected at a mixing junction at first ends and communicating with said storage means and an output of said first pump assembly at second respective ends thereof, said first ends commonly communicating with an input to said second pump assembly.

6. A fluid diluter as claimed in claim 5, further comprising at least two diluent conduits which communicate with said fluid conduit at locations preceding said mixing junction.

7. A fluid diluter as claimed in claim 1, further comprising a hydrodynamic focusing device including one of an inducting tube and a director, said focusing device having first and second ends, said first end communicating with said storage means, said focusing device having a focusing chamber communicating with an output of said first pump assembly, said focusing chamber having an aperture at which said second end of said one of an inducting tube and a director is directed, said aperture communicating said focusing chamber with said receiving conduit.

8. A fluid diluter as claimed in claim 1, including valve means for regulating flow to and from said first and second pump assemblies.

9. A fluid diluter as claimed in claim 8, wherein said valve means comprises one of a shut off valve and a non-return valve.

10. A fluid diluter as claimed in claim 1, wherein said pump assemblies are differentially actuated by a common actuator.

11. In combination:
    a particle analyzer; and
    a fluid diluter comprising:
        at least first and second pump assemblies with different pumping capacities for a given pump cycle, each of said pump assemblies having a charge stroke and a deliver stroke,
        storage means for containing fluid to be diluted,
        a first conduit for connection to a diluent supply,
        mixing means arranged to receive said fluid and said diluent and to form a mixed fluid, said first pump assembly being arranged to pump said diluent to said mixing means,
        a receiving conduit for said mixed fluid communicating with said second pump assembly,
        said delivery stroke of said first pump assembly being arranged to coincide with said charge stroke of said second pump assembly, such that fluid to be diluted is drawn out of said storage means by said second pump assembly as said diluent is pumped,
        said first and second pump assemblies in turn comprising first and second cylinders and respective first and second pistons therein, said first and second pistons each being sealed with a respective one of said first and second cylinders only at one predetermined portion of said respective cylinder, said first and second pistons being mounted integrally with a common actuator rod connected between them so as not to be movable relative to one another;

said fluid diluter further comprising a hydrodynamic focusing device including one of an inducting tube and a director, said focusing device having first and second ends, said first end communicating with said storage means, said focusing device having a focusing chamber communicating with an output of said first pump assembly, said focusing chamber having an aperture at which said second end of said one of an inducting tube and a director is directed, said aperture communicating said focusing chamber with said receiving conduit;

wherein said particle analyzer is positioned to analyze said mixed fluid.

12. The combination of claim 11, further comprising analyzer electrodes located respectively upstream and downstream of said aperture of said focusing chamber of said focusing device.

* * * * *